US008425598B2

(12) United States Patent
Klink et al.

(10) Patent No.: US 8,425,598 B2
(45) Date of Patent: Apr. 23, 2013

(54) IMPLANTABLE SYSTEM FOR RESTORING ACCOMMODATION CAPACITY USING INTERNAL ENERGY

(75) Inventors: Simon Klink, Pohlheim (DE); Georg Bretthauer, Karlsruhe (DE); Rudolf Guthoff, Rostock (DE); Mark Bergemann, Göppingen (DE)

(73) Assignee: Karlsruher Institut fuer Technologie, Karlsruhe (DE)

( * ) Notice: Subject to any disclaimer, the term of this patent is extended or adjusted under 35 U.S.C. 154(b) by 76 days.

(21) Appl. No.: 12/992,266

(22) PCT Filed: May 14, 2009

(86) PCT No.: PCT/EP2009/055854
§ 371 (c)(1),
(2), (4) Date: Jan. 26, 2011

(87) PCT Pub. No.: WO2009/138468
PCT Pub. Date: Nov. 19, 2009

(65) Prior Publication Data
US 2011/0125259 A1   May 26, 2011

(30) Foreign Application Priority Data

May 15, 2008   (DE) .......................... 10 2008 023 726

(51) Int. Cl.
*A61F 2/16* (2006.01)
*A61F 2/14* (2006.01)

(52) U.S. Cl.
USPC .......... 623/6.37; 623/4.1; 623/6.22; 623/6.23

(58) Field of Classification Search ................... 623/4.1, 623/6.22, 6.37, 6.23
See application file for complete search history.

(56) References Cited

U.S. PATENT DOCUMENTS

| | | | |
|---|---|---|---|
| 4,373,218 | A | 2/1983 | Schachar |
| 5,476,514 | A | 12/1995 | Cumming |
| 6,096,078 | A | 8/2000 | McDonald |
| 6,120,538 | A | 9/2000 | Rizzo, III et al. |
| 6,369,954 | B1 | 4/2002 | Berge et al. |
| 6,485,516 | B2 | 11/2002 | Boehm |
| 6,638,304 | B2 | 10/2003 | Azar |

(Continued)

FOREIGN PATENT DOCUMENTS

| | | |
|---|---|---|
| DE | 19904441 C1 | 9/2000 |
| DE | 10062218 A1 | 7/2001 |

(Continued)

OTHER PUBLICATIONS

Schneider, H. et al.: Evidence-based observations on accommodative artificial lenses, $102^{nd}$ Annual Convention of the German Ophthalmological Society, Berlin, Germany (Sep. 23-26, 2004).

(Continued)

*Primary Examiner* — Thomas J Sweet
*Assistant Examiner* — Krutanjali M Shah
(74) *Attorney, Agent, or Firm* — Abel Law Group, LLP.

(57) ABSTRACT

An implantable system for restoring accommodation capacity includes at least one ring configured to be implanted in a ciliary sulcus and a capacitor with a first capacitor plate and a second capacitor plate. The first capacitor plate is arranged on an implantable ring and the second capacitor plate is connected to a capsular bag.

16 Claims, 2 Drawing Sheets

U.S. PATENT DOCUMENTS

| | | |
|---|---|---|
| 6,645,245 B1 | 11/2003 | Preussner |
| 2002/0149743 A1 | 10/2002 | Portney |
| 2004/0181279 A1 | 9/2004 | Nun |
| 2004/0215340 A1 | 10/2004 | Messner et al. |
| 2005/0085907 A1 | 4/2005 | Hanna |
| 2005/0113912 A1 | 5/2005 | Feenstra et al. |
| 2005/0137703 A1 | 6/2005 | Chen |
| 2005/0256571 A1 | 11/2005 | Azar |
| 2007/0260307 A1 | 11/2007 | Azar |
| 2008/0306589 A1 | 12/2008 | Donitzky et al. |
| 2009/0105817 A1 | 4/2009 | Bretthauer et al. |
| 2010/0237744 A1 | 9/2010 | Koker et al. |

FOREIGN PATENT DOCUMENTS

| | | |
|---|---|---|
| DE | 20111320 U1 | 10/2001 |
| DE | 9422429 U1 | 1/2002 |
| DE | 10125829 A1 | 11/2002 |
| DE | 10139027 | 2/2003 |
| DE | 10155345 A1 | 5/2003 |
| DE | 102004025603 A1 | 12/2005 |
| DE | 102005038542 A1 | 2/2007 |
| DE | 10 2007 008375.2 | 10/2008 |
| EP | 1 726 272 A1 | 11/2006 |
| WO | WO99/18456 A1 | 4/1999 |
| WO | WO 02/083033 A2 | 10/2002 |
| WO | WO03/017873 A1 | 3/2003 |
| WO | WO03/069380 A1 | 8/2003 |
| WO | WO2006/050171 A2 | 5/2006 |

OTHER PUBLICATIONS

Kammann, J. et al.: Empirical Results Regarding Accommodative Lenses, Current Aspects of Human Accommodation, Publishers: Guthoff, R. et al., Ludwig K. Kaden Verlag, Heidelberg, pp. 163-170 (2001).

Fine, H. et al.: Technology generates IOL with amplitude of accommodation, Ophthalmology Times Special Report (Mar. 15, 2005).

Lavin, M. et al.: Multifocal intraocular lenses—part 1, Optometry Today May 2001, pp. 34-37 (2001).

Lavin, M.: Multifocal intraocular lenses—part 2, Optometry Today Aug. 2001, pp. 43-44 (2001).

Nishi, O. et al.: Controlling the Capsular Shape in Lens Refilling, Archives of Ophthalmology 115(4), pp. 507-510 (1997).

Fine, I.H.: The SmartLens—a fabulous new EOL technology, Eye World 7(10) (2002).

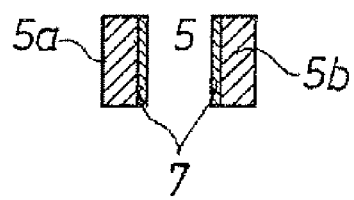
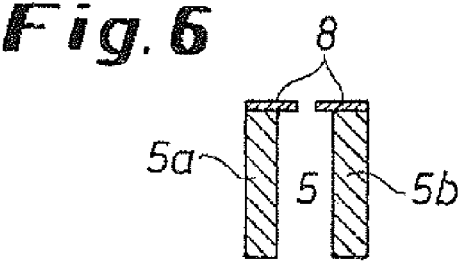
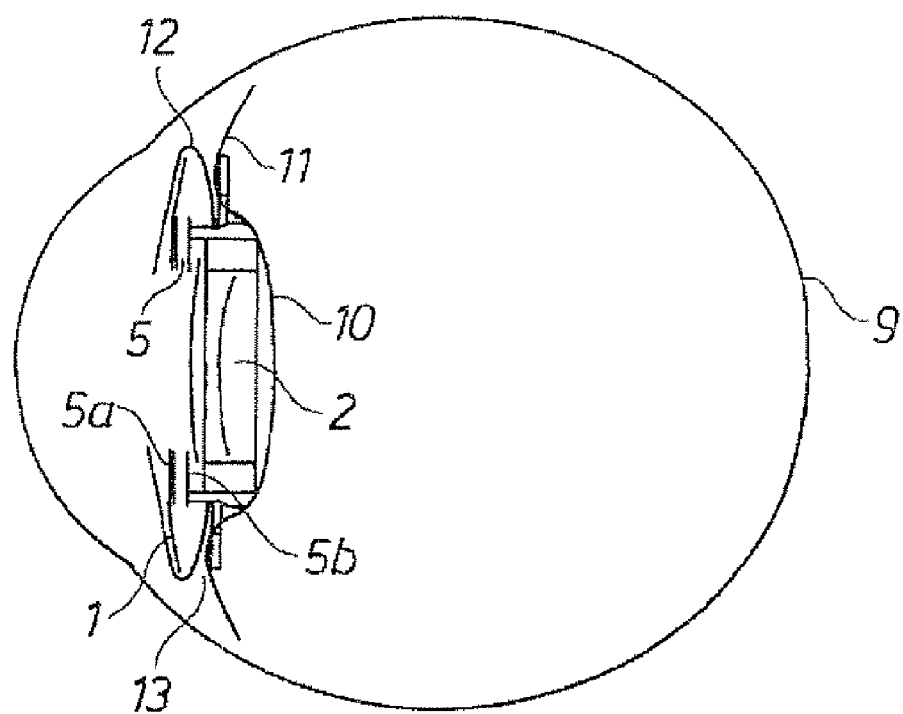

IMPLANTABLE SYSTEM FOR RESTORING ACCOMMODATION CAPACITY USING INTERNAL ENERGY

CROSS REFERENCE TO PRIOR APPLICATIONS

This application is a U.S. National Phase application under 35 U.S.C. §371 of International Application No. PCT/EP2009/055854, filed on May 14, 2009 and which claims benefit to German Patent Application No. 10 2008 023 726.4, filed on May 15, 2008. The International Application was published in German on Nov. 19, 2009 as WO 2009/138468 A1 under PCT Article 21(2).

FIELD

The present invention provides an accommodation system that can be implanted in or on the eye to restore accommodation capacity using internal energy.

BACKGROUND

The human eye is an optical system that forms a sharp image of objects on the retina with the aid of a number of refractive interfaces. In doing so, the light waves pass through the cornea, the aqueous humor in the anterior chamber (camera anterior bulbi), the crystalline lens (lens crystallina) and the vitreous body in the posterior chamber (camera vitrea bulbi), which all have different refractive indices. If the distance from the viewed object changes, it is necessary for the imaging behavior of the optical system to change in order to ensure that an image with the same sharpness is formed on the retina. The human eye does this by altering the shape of the lens with the aid of the ciliary muscle (musculus ciliaris), as a result of which the shape and the position of the anterior and posterior surfaces of the lens change substantially, this being referred to as accommodation. In an intact accommodation system in a young person, the vertex power of the system can in this way change between the remote setting (unaccommodated state) and the near setting (accommodated state) by 14 diopters (accommodation range). Therefore, in a young person with normal sight (emmetropic), objects located between the far point, which is at infinity, and the near point, which is about 7 cm in front of the cornea, can be imaged sharply on the retina.

Since the accommodation capacity of the human eye decreases with age, a number of implantable artificial lens systems with variable focal length have been developed.

Potentially accommodative intraocular lenses are lenses or lens systems which are inserted in place of the natural lens, after the latter has been surgically removed, and which are mainly secured in the capsular bag. By means of a still existing but weak residual contraction of the ciliary muscle, a haptic is intended to permit an axial movement of the lens.

Devices for restoring accommodation capacity have, for example, been described in DE 101 55 345 C2, U.S. Pat. No. 6,638,304 B2, WO 03/017873 A1, U.S. Pat. No. 4,373,218, DE 94 22 429 U1, DE 201 11 320 U1, DE 100 62 218 A1, DE 10139027, WO 02/083033, DE 10125829 A1, US 2004/0181279 A1, US 2002/0149743 and U.S. Pat. No. 6,096,078.

Numerous scientific publications relating to the topic of accommodation capacity of lens systems also exist. Reference is made by way of example to the following publications:

Schneider, H.; Stachs, O.; Guthoff, R.: Evidenzbasierte Betrachtungen zu akkommodativen Kunstlinsen [Evidence-based observations on accommodative artificial lenses], 102nd Annual Convention of the German Ophthalmological Society (Berlin, Germany, Sep. 23-26, 2004) (2004); Kammann, J.; Dornbach, G.: Empirical results regarding accommodative lenses, Current Aspects of Human Accommodation, publishers: Guthoff, R.; Ludwig, K. Kaden Verlag Heidelberg (2001), pages 163-170; Fine, H.; Packer M.; Hoffmann R.: Technology generates IOL with amplitude of accommodation (Ophthalmology Times Special Report, March 15, 2005) (2005); Lavin, M.: Multifocal intraocular lenses—part 1, Optometry Today May 2001 (2001), pages 34-37; Lavin, M.: Multifocal intraocular lenses—part 2; Optometry Today August 2001 (2001), pages 43-44; Nishi, O.; Nishi, K.; Mano, C.; Ichihara, M.; Honda, T.: Controlling the capsular shape in lens refilling, Archives of Ophthalmology 115(4) (1997), pages 507-510; and Fine, I. H.: The SmartLens—a fabulous new IOL technology, Eye World 7(10) (2002).

Systems have already been proposed which use the axial prestressing of the capsular bag to convert an axial movement into a change in refractive power using contraction of the ciliary muscle. For example, it is proposed to use the pressure of the rearwardly deflected capsular bag in order to press a gel partly through an apertured diaphragm and thus influence the radius of curvature of the gel swelling out on the other sides. In this system, however, it has not yet been possible to demonstrate the lasting stability of a gel present in the aqueous humor, nor the satisfactory optical properties of the gel pressed through a diaphragm.

DE 199044441 C1 describes fitting magnets on the capsular bag and on the eyeball to deflect the capsular bag forward and, with contraction of the ciliary muscle, still further forward. The IOL (intraocular lens) fixed in the capsular bag is moved along with this and thus causes a change in the vertex power. With this system being placed in the aqueous humor, the axial travel is limited to as far as the iris and is not sufficient to generate the necessary vertex power in an emmetropic eye with the ciliary muscle relaxed.

German patent application DE 10 2007 008 375.2 describes an active mechatronic system which determines the accommodation requirement and, with the aid of electronics, adjusts an optical system of variable focal length. Such a system with a measuring unit and control electronics must additionally have an energy supply system. The energy supply unit must be able to cover the routine consumption of measuring device, control electronics and optical system. A miniaturized energy supply system sufficient for these purposes and able to cover the power requirement of the electronics is, however, not yet available.

DE 10 2005 038 542 A1 describes a device for restoring accommodation capacity, comprising:
  at least one optical system,
  at least one data acquisition system for recording the endogenous control signals for pupil diameter or eye movement or accommodation or a combination of the controlled control signals,
  at least one data processing system for generating a regulating signal for the optical system from the recorded endogenous control signals,
  at least one energy supply system, and
  at least one securing system.

Therefore, this device requires a data acquisition system and an energy supply system.

U.S. Pat. No. 6,120,538 describes, similar to DE 10 2005 038 542 A1, a system with means for processing measured data (range-finder 18 and controller 16) and with a separate energy source (20).

Ophthalmology is still faced with the problem that, from the age of about 45 years, the ability of the human eye to accommodate (adjust the refractive power of the actual lens) sufficiently to a reading distance of about 30 cm decreases. In principle, the artificial lens implanted in a cataract extraction is still unable to focus to different distances. For biological reasons, previous attempts at using intraocular structures, in particular the ciliary muscle activity within the capsular bag, to mechanically change the refractive power of implantable systems have been unsuccessful, nor is this expected to be achieved in the near future.

SUMMARY

An aspect of the present invention is to provide an implantable system which converts the activity of the ciliary muscle but is not reliant on the deformability of the capsular bag. A further aspect of the present invention is to provide an autonomous system that can operate without an external energy supply.

In an embodiment, the present invention provides an implantable system for restoring accommodation capacity which includes at least one ring configured to be implanted in a ciliary sulcus and a capacitor with a first capacitor plate and a second capacitor plate. The first capacitor plate is arranged on an implantable ring and the second capacitor plate is connected to a capsular bag.

BRIEF DESCRIPTION OF THE DRAWINGS

The present invention is described in greater detail below on the basis of embodiments and of the drawings in which:

FIG. 5 shows how coatings 7 are applied between the capacitor plates 5a, b specifically upon said plates;

FIG. 6 shows an example of the arrangement of spacers 8; and

FIG. 7 shows the eyeball 9 with the implanted system according to the present invention.

DETAILED DESCRIPTION

Figure 1:
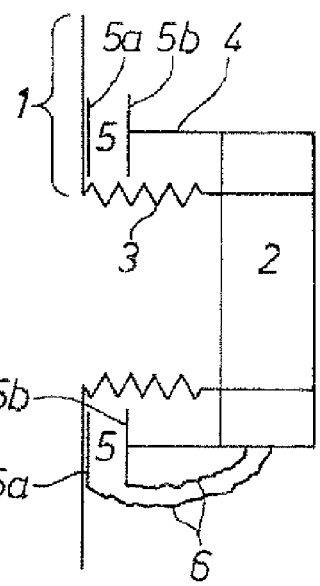
FIG. 1 shows a schematic representation of the system according to the present invention.

In an embodiment of the present invention, the second plate can, for example, be connected to the capsular bag.

This system is accordingly used for implantation in or on the eye for the purpose of restoring accommodation capacity using internal energy.

The ciliary muscle contracts even in persons with presbyopia or in persons who have undergone cataract surgery. In this way, the elastically prestressed zonular fibers distributed radially around the capsular bag are relaxed. Under the effect of an artificial force acting on the capsular bag in the direction of the optic axis, a shifting of the capsular bag takes place along the optic axis upon movement of the ciliary muscle.

In an embodiment of the present invention, this external force can be supported by a ring that can be implanted in the ciliary sulcus. The external diameter of the ring corresponds to the internal diameter of the ciliary sulcus and is over 8 mm. The external diameter of the ring can, for example, be between 8 and 20 mm, between 10 and 18 mm, or between 12 and 16 mm. The external diameter of the ring can also, for example, be 14±0.5 mm. The internal diameter of the ring can, for example, be 0.5 to 8 mm, between 0.8 and 2.5 mm, or between 1.0 and 1.5 mm smaller than the external diameter.

By virtue of the arrangement of the ring, it is possible to fit a capacitor in this area in front of the capsular bag. The capacitor can, for example, be ring-shaped. One plate of the capacitor can be arranged on the implanted ring, and the other can be connectable or connected mechanically to the system in the capsular bag.

When a defined charge is applied to the capacitor plates, the position of the capsular bag along the optic axis changes with the movement of the ciliary muscle. In this way, the plate spacing of the capacitor can also change, which can result in a change of voltage on the latter.

In an embodiment of the present invention, an active optical element can be implanted in the capsular bag and can, for example, be connected electrically to the capacitor. This element can, for example, be an electrowetting module. In such a case, the change in geometry can be obtained through influencing the contact angle (electrowetting): two immiscible fluids of approximately the same density, which differ in terms of their refractive indices, form a spherically curved or plane interface (meniscus). When the one fluid that is electrically conductive is brought into contact with an electrode and a potential difference is applied to an electrode separated from a second of the two fluids by an insulating layer (dielectric), the contact angle and thus the curvature of the meniscus can be changed by the electrowetting effect. Since the meniscus separates two media of different refractive index, the optical imaging behavior can be changed. WO 99/18456 describes an axial arrangement of conductive fluid, transparent dielectric and transparent electrode in the beam path and measures for radially centering the drop in the optic axis. WO 03/069380 describes an arrangement in which the electrode coated with a dielectric is arranged cylindrically about the optic axis. The electrically conductive fluid and the insulating fluid are arranged axially one after another on the optic axis, in any desired sequence, along with the meniscus separating the two.

With the electrowetting module, therefore, the curvature of a spherical interface between a conductive fluid and a non-conductive fluid can, for example, be influenced by a change in voltage or charge on the, for example, cylindrical outer surface. If the two fluids have different refractive indices, the vertex power of the eye is thus also changed, which is equivalent to the desired change in focal position. If the electrowetting module and the capacitor are electrically connected, a movement of the ciliary muscle leads to a change in the focal position. The original biological relationship can thereby be restored. Once the capacitor has been charged, the system according to the present invention functions without or with only a low energy supply. The plate spacing of the capacitor and the charging thereof should thereby be adapted to the charge/voltage properties of the electrowetting module.

In principle, all electrostatic actuator concepts with a low energy requirement are suitable, such as concepts in which, for example, electric charges are shifted but are not consumed or are only consumed to a very slight extent. Available principles for changing the refractive power are, for example:

1. Electrowetting; and
2. Combinations of purely potential-driven actuators without permanent current, such as a conductive polymer actuator, an electrostatic polymer actuator, a nanotube actuator as described in DE 10 2004 025 603 A1, a piezoceramic actuator, and optical principles based on shift, displacement or deformation etc., such as an axially shiftable lens, a laterally shiftable cubic lens pairs, a fluid lens, an elastic lens, and all systems that can be operated with an abovementioned actuator.

According to an embodiment of the present invention, a high charge capacity can be achieved, for example, by use of a filling medium with a high dielectric constant. The filling medium can, for example, have a low conductivity (imaginary permittivity), a high real permittivity (dielectric constant), a low viscosity, and a high degree of biocompatibility. Examples are hydrocarbons such as dimethyl ether, ethanol, glycol, propanol, etc. The filling medium is not absolutely essential to the function.

Contact between the plates can lead to short-circuits. Special devices can be provided according to an embodiment the present invention to avoid such short-circuits. In the simplest case, insulation can be provided. For example, the plates can be provided with an insulating layer. For example, a coating of ceramic or plastic. The material should be chemically inert to the environment.

Another embodiment involves the use of spacers, which can be insulating or also non-insulating.

By means of additional elastic elements, such as suitable spring elements, it is possible to compensate for the force of attraction between the capacitor plates.

Further springs or spring-shaped elements can serve for the deflection of the optical system.

According to an embodiment of the present invention, transparent materials of similar density can be used in the electrowetting module. This provides the optical properties of the system. As it is possible to choose the capacitance and charge of the capacitor, a sufficient accommodation range can be achieved even with a short axial travel. By virtue of the use of the capacitor and the direct electrical connection to the electrowetting module, this system according to the present invention can function without external energy supply. This signifies an energy supply exclusively by internal means, for example, with solar cells in the eye or oscillation elements with external excitation.

The configuration of the artificial accommodation system without external energy supply makes the system easier to produce and reduces the probability of failure. It nevertheless provides good optical properties and can be adapted to different patients, such that a sufficient accommodation range can be provided. This combination of advantages is provided by the use of a ring capacitor and by the direct electrical connection to an electrowetting module positioned in the capsular bag. The conversion of the ciliary muscle contraction to an accommodation requirement can be predefined in a number of ways through the force-travel profile of the axial prestressing of the capsular bag.

The present invention is explained in more detail below with reference to the Figures.

FIG. 1 shows a schematic representation of the system according to the present invention. It shows the ring 1 that can be implanted in the ciliary sulcus, and the electrowetting module 2. Alternatively, this can be an optical system with an actuator driven by voltage.

The system comprises springs 3 for rearward deflection of the optical system in the capsular bag. A rigid connection 4 is present between the optical system and a capacitor plate 5b of the capacitor 5. The capacitor 5 has a variable plate spacing, the second capacitor plate 5a being connected to the implantable ring 1. Capacitor 5 and optical system are closed together by the electrical connection 6.

Figure 2:
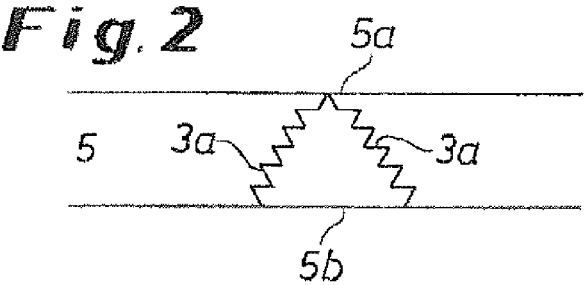
FIG. 2 shows the elastic element 3a in detail.

FIG. 2 shows the elastic element 3a in detail, with which the force of attraction between the capacitor plates 5a,b of the capacitor 5 can be compensated. This element can be present as a non-linear spring or in a non-linear arrangement in order to increase the travel in the plate spacing.

Figure 3:
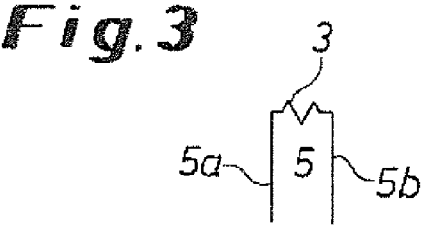
FIG. 3 shows a variant of the spring element 3a between the capacitor plates 5a,b for compensation of the electrostatic attraction.

FIG. 3 shows a variant of the spring element 3a between the capacitor plates 5a,b for compensation of the electrostatic attraction.

Figure 4:
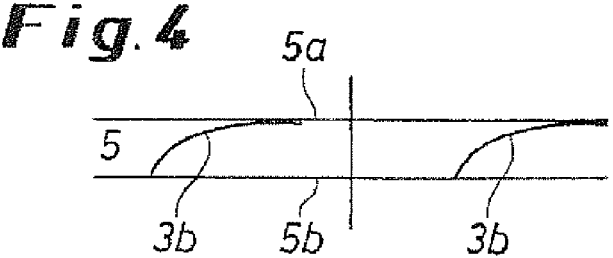
FIG. 4 shows circularly distributed ring springs 3b.

FIG. 4 shows circularly distributed ring springs 3b.

FIG. 5 shows how, in order to avoid short-circuits, coatings 7 are applied between the capacitor plates 5a, b specifically upon said plates. These coatings 7 are not electrically conductive.

FIG. 6 shows an example of the arrangement of spacers 8. These spacers 8 can be insulated or can themselves be made of insulating material.

FIG. 7 shows the eyeball 9 with the implanted system according to the present invention. Zonular fibers 11 are distributed radially around the capsular bag 10. A ring 1 is implanted in the ciliary sulcus 12. A ring-shaped plate capacitor 5 is mounted on the ring 1. One plate 5a is arranged on the implanted ring 1, and the other plate 5b is arranged on the capsular bag 10. An electrowetting module 2 is implanted in the capsular bag 10. When the electrowetting module 2 and the ring capacitor 5 are electrically connected, the movement of the ciliary muscle 13 leads to a change in focal position.

The present invention is not limited to embodiments described herein; reference should be had to the appended claim.

The invention claimed is:

1. Method of using an implantable system for restoring accommodation capacity, the method comprising:
    providing the implantable system comprising:
        at least one ring configured to be implanted in a ciliary sulcus, and
        a capacitor with a first capacitor plate and a second capacitor plate, wherein the first capacitor plate is arranged on an implantable ring and the second capacitor plate is adapted to be connected to a capsular bag; and
    implanting the implantable system on or in the human eye so as to restore accommodation capacity using internal energy.

2. An implantable system for restoring accommodation capacity, the system comprising:
    at least one ring configured to be implanted in a ciliary sulcus; and
    a capacitor with a first capacitor plate and a second capacitor plate, wherein the first capacitor plate is arranged on an implantable ring and the second capacitor plate is adapted to be connected to a capsular bag.

3. The system as recited in claim 2, wherein the implantable ring has a diameter of 8 to 20 mm.

4. The system as recited in claim 2, wherein the capacitor is ring-shaped.

5. The system as recited in claim 2, further comprising an active optical element configured to be implanted in the capsular bag.

6. The system as recited in claim 5, wherein the active optical element is an electrowetting module.

7. The system as recited in claim 5, wherein the active optical element and the capacitor are electrically connected.

8. The system as recited in claim 2, wherein the system further comprises a filling medium.

9. The system as recited in claim 8, wherein the filling medium has a high dielectric constant.

10. The system as recited in claim 5, further comprising devices configured to avoid short-circuits caused by contact between the first capacitor plate and the second capacitor plate.

11. The system as recited in claim 10, wherein the first capacitor plate and the second capacitor plate include an insulating layer.

12. The system as recited in claim 10, wherein the devices are at least one of a spring element, an insulating layer configured to be non-electrically conductive and spacers.

13. The system as recited in claim 12, wherein the spacers are at least one of insulated, made of an insulating material and non-insulated.

14. The system as recited in claim 12, wherein the spacers are configured to avoid a contact between the first capacitor plate and the second capacitor plate.

15. The system as recited in claim 12, wherein the at least one spring element is configured to counteract an attraction of the first capacitor plate and the second capacitor plate.

16. The system as recited in claim 12, wherein the at least one spring element is configured to deflect the capsular bag.

* * * * *